United States Patent                    (10) Patent No.:     US 9,504,449 B2
Nicolas et al.                                       (45) Date of Patent:        Nov. 29, 2016

(54) ULTRASONIC IMAGING DEVICE WITH IMAGE ACQUISITION RATE OPTIMIZATION

(75) Inventors: Jean-Marie Nicolas, Rueil Malmaison (FR); Laurent Kopp, Turin (IT); Frédéric Mosca, Chateauneuf la Rouge (FR); Claude Cohen-Bacrie, Puyricard (FR); Christophe Fraschini, Aix en Provence (FR)

(73) Assignee: SUPER SONIC IMAGINE, Aix en Provence (FR)

( * ) Notice: Subject to any disclaimer, the term of this patent is extended or adjusted under 35 U.S.C. 154(b) by 597 days.

(21) Appl. No.: 13/984,011

(22) PCT Filed: Feb. 3, 2012

(86) PCT No.: PCT/EP2012/051900
§ 371 (c)(1),
(2), (4) Date: Oct. 8, 2013

(87) PCT Pub. No.: WO2012/107370
PCT Pub. Date: Aug. 16, 2012

(65) Prior Publication Data
US 2014/0024943 A1    Jan. 23, 2014

(30) Foreign Application Priority Data
Feb. 7, 2011 (FR) ...................... 11 50966

(51) Int. Cl.
*A61B 8/08*    (2006.01)
*G01S 15/89*   (2006.01)
(Continued)

(52) U.S. Cl.
CPC ............ *A61B 8/5207* (2013.01); *A61B 8/145* (2013.01); *A61B 8/4483* (2013.01); *A61B 8/469* (2013.01); *A61B 8/54* (2013.01); *G01S 15/8959* (2013.01);
(Continued)

(58) Field of Classification Search
None
See application file for complete search history.

(56) References Cited

U.S. PATENT DOCUMENTS 6,048,315 A    4/2000 Chiao et al.

OTHER PUBLICATIONS

Jian, Shen et al. A New Coded-Excitation Ultrasound Imaging System—Part I: Basic Principles. IEEE Transactions on Ultrasound, Ferroelectrics and Frequency Control, Jan. 1, 1996, vol. 43, No. 1, pp. 131-140.
Jensen, J. A. et al. Synthetic aperture ultrasound imaging. Ultrasonics, IPC Science and Technology Press Ltd., Dec. 22, 2006, vol. 44, pp. E5-E15.
Misaridis, T. et al. Use of modulated excitation signals in medical ultrasound, Part III: High frame rate imaging. IEEE Transactions on Ultrasonics, Ferroelectrics and Frequency Control, Feb. 1, 2005, vol. 52, No. 2, pp. 208-219.
(Continued)

*Primary Examiner* — Serkan Akar
(74) *Attorney, Agent, or Firm* — MH2 Technology Law Group, LLP (57) ABSTRACT

The disclosure includes a method of acquiring high-resolution ultrasound images using an array of transducers using successive transmission matrices. Implementations include operations for determining inter-transducer correlation matrices of an area of interest and an unwanted area; determining a characteristic matrix of the area of interest from the product of the inverse of the inter-transducer correlation matrix of the unwanted area and the inter-transducer correlation matrix of the area of interest; calculating eigenvectors and values of the characteristic matrix to define a transmission matrix; adjusting the image acquisition rate and image quality in order to define eigenvectors for firing; multiplying a reception matrix comprising the acquired signals completed by data set to zero corresponding to the firings not effected by the inverse of the transmission matrix to obtain a complete data set; reconstructing a high-resolution image of the area of interest as in synthetic aperture echographic imaging methods.

13 Claims, 8 Drawing Sheets

(51) Int. Cl.
*A61B 8/14* (2006.01)
*A61B 8/00* (2006.01)

(52) U.S. Cl.
CPC ........ *G01S 15/8977* (2013.01); *G01S 15/8997* (2013.01); *A61B 8/485* (2013.01)

(56) References Cited

OTHER PUBLICATIONS

Slepian, D. Prolate Spheroidal Wave Functions, Fourier Analysis, and Uncertainty—V: The Discrete Case. Bell System Technical Journal, American Telephone and Telegraph Co., Jan. 1, 1978, vol. 57, No. 5, pp. 1371-1430.

ULTRASONIC IMAGING DEVICE WITH IMAGE ACQUISITION RATE OPTIMIZATION

CROSS-REFERENCE TO RELATED APPLICATIONS

This application is a U.S. National Stage application of International Application No. PCT/EP2012/051900 filed Feb. 3, 2012, which claims priority to French patent Application No. 1150966 filed Feb. 7, 2011, the entire disclosures of which are hereby incorporated herein by reference in their entireties.

BACKGROUND OF THE INVENTION

The field of the invention is that of echographic imaging. The invention relates to methods and devices for imaging and treating pathologies of human organs.

It relates more particularly to methods and devices for imaging with high spatial and temporal resolution based on the use of synthetic methods. The temporal resolution increases as the number of firings necessary to reconstruct the image decreases. The image acquisition rate, i.e. the number of images per unit time, is directly related to this temporal resolution.

Standard echographic imaging systems utilize the echoes backscattered by the medium to be probed, generally a biological tissue, to analyze the variations in acoustic impedance characteristic of biological structures and thus to reconstruct an image of that medium.

Figure 1:
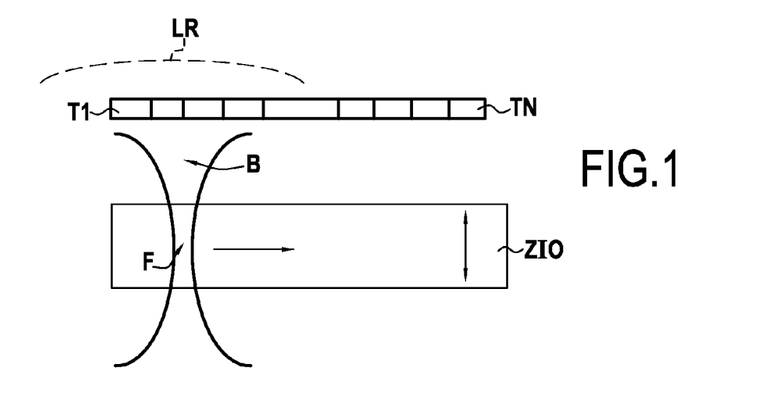
FIG. 1 shows diagrammatically the operation of a mode B echograph.

An ultrasound image is typically obtained by generating and transmitting beams focused at a given focal distance and transmitted in a given direction to produce what is referred to as a line of the image. This is shown in FIG. 1, in which a delay law LR diagrammatically represented by a dashed line curve is applied to an array of transducers T1 to TN. This generates a beam B focused around a point F. Transverse scanning, diagrammatically represented by an arrow, is effected over the length of the array of transducers. The corresponding line of the image is then reconstructed by focusing the received signals. The whole image is obtained by transverse scanning of the area of interest using successively offset imaging lines. An optimum imaging area ZIO is then observed.

This imaging method generally uses matrix, linear, or curved echographic probes comprising a plurality of transducers, for example piezoelectric elements, used for transmission and reception. These transducers are controlled individually via independent electronic channels capable of applying to them electrical signals delayed relative to one another. Transmission focusing is effected by applying delays to the various signals transmitted. These delays correspond to the time of flight differences between the various antenna elements and the focal point, thus creating the acoustic equivalent of a lens.

Thereafter, dynamic focusing laws, i.e. a delay law for each reconstructed pixel, are used on reception to isolate the acoustic signatures coming from a given location of the medium and reconstituting its acoustic image. This is known as beamforming.

This method, which is very widely used in commercial systems, is called the mode B method. Image quality is optimum for depths close to the focal distance but is degraded on moving away from the focal spot.

The number of characteristic firings to produce such an image is generally equal to the number of reconstructed lines and is of the same order of magnitude as the number of antenna elements, typically 128 or 256.

Variants of this method have been developed.

Figure 2:
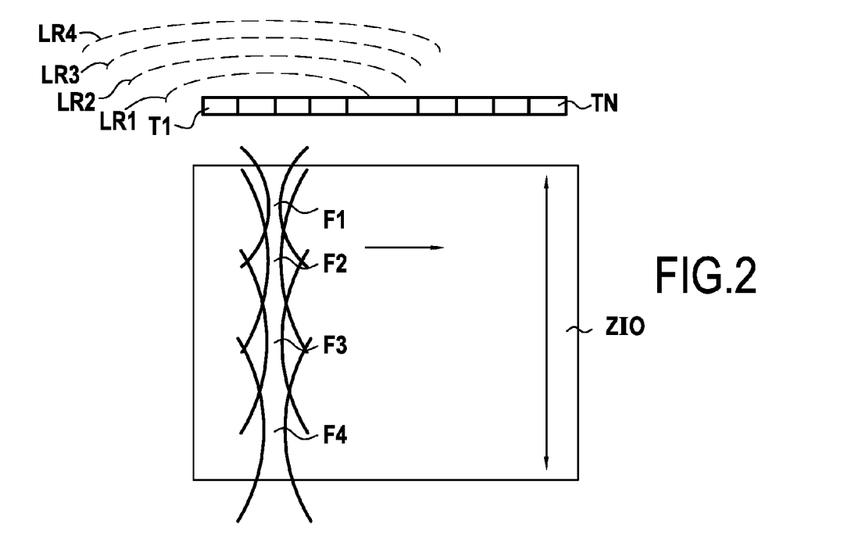
FIG. 2 shows diagrammatically the operation of a multi-focus mode echograph.

The depth multi-focus method consists in determining a plurality of focal distances and reconstructing the line portions situated in the vicinity of the various focal points. This method improves image quality but increases the number of firings necessary by a factor $N_{foc}$ that is the number of focal distances used. This is shown in FIG. 2 and described in U.S. Pat. No. 5,113,706. Successive delay laws LR1 to LR4 are transmitted, each generating a beam focused at a different point F1 to F4. It is seen that a wider optimum imaging area is obtained.

Figure 3A:
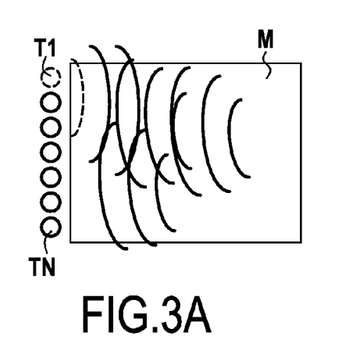
FIG. 3 shows diagrammatically the operation of an echograph acquiring a complete data set.
Figure 3B:
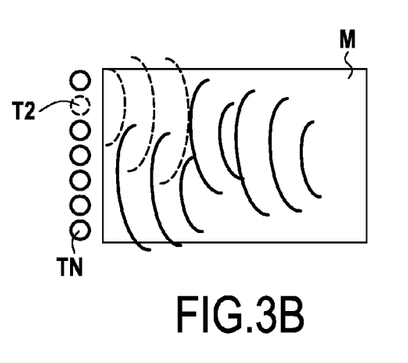

The synthetic transmit aperture method consists in transmitting unfocused beams emanating successively from each of the elements of the antenna and then reconstructing for each of the firings a so-called "low resolution" image by reception focusing. This is shown in FIG. 3. In FIG. 3A, a first antenna element transmits a wave towards a diffusing medium M. The signal is diffused and reflected by the medium. Then, in FIG. 3B, a second antenna element T2 transmits the same wave toward the medium M, and so on for all of the antenna elements T1 to TN.

The data set acquired after transmission from each of the antenna elements T1 to TN in succession is called the complete data set. The final image is obtained by summing the partial images coherently in amplitude and in phase, which images are referred to as "low resolution" images. In contrast to a standard imaging mode, an image is obtained with dynamic transmission focusing, which focusing is synthetic. It is for this reason that the term synthetic transmit aperture is used. The image obtained in this way is of optimum quality and the number of firings necessary is equal to the number of antenna elements.

The above method has the major drawback of not enabling areas that are too far from the antenna to be imaged. The ratio between the signal and the thermal noise caused by the sensors is lower than for the standard method by a factor $\sqrt{N_{el}}$, $N_{el}$ being the number of the elements of the antenna. This is because, for imaging the same pixel, the standard method requires only one acquisition, whereas the coherent synthesis method requires the acquisition of $N_{el}$ firings, that is to say, for Gaussian white noise, $\sqrt{N_{el}}$ times more noise. This is described in U.S. Pat. No. 5,623,928 and in U.S. Pat. No. 4,604,697.

To alleviate the problem of the signal-to-noise ratio of synthetic aperture imaging, a so-called spatial coding approach has been developed. This is based on defining and using a transmission matrix. The transmission matrix is defined by concatenating the various weighting laws of the antenna during successive transmissions.

In the special case of acquiring the complete data set, the transmission matrix used is the identity matrix.

Figure 4:
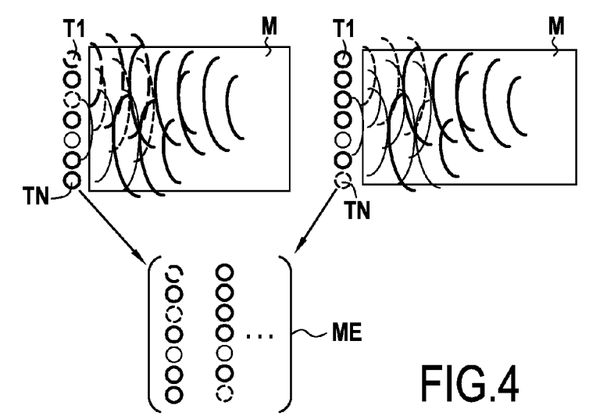
FIG. 4 shows diagrammatically the operation of an echograph using spatial coding.

The spatial coding method consists in sounding the medium with the weighting laws contained in the transmission matrix, chosen beforehand to be reversible. This is shown in FIG. 4 where it is seen that each of the transducers T1 to TN transmits with a different but predefined intensity. The intensities for each firing constitute a vector of a transmission matrix ME grouping the successive intensities at each transducer. The signals acquired in this way are then projected into the so-called canonic base, i.e. each matrix composed of signals received by the transducers at a given time during the transmission-acquisition process is leftward multiplied by the inverse of the transmission matrix.

This technique enables the complete data set to be acquired from a transmission matrix ME that is different from the identity matrix. To be more precise, any transmission matrix may be used on condition that it may be inverted.

The major benefit of this technique is that it enables improvement of the signal-to-noise ratio of the synthetic aperture imaging method by a factor equal to the determinant of the transmission matrix.

This method, initially introduced by Chiao, notably in U.S. Pat. No. 6,048,315, in the context of medical ultrasound, as mainly used with Hadamard transmission matrices. These are easier to implement and they make optimum signal-to-noise ratios possible.

The aperture synthesis and incoherent summing methods are sometimes used simultaneously, for example as in document US 2003/0149257.

A synthesis method that is not based on the transmission matrix consists in coherent summing of images formed from transmissions of unfocused depointed waves. Here a delay law is applied such that the wave front is at a predetermined angle to the surface of the probe. In this way, the transmitted wave propagates in a direction at a particular angle to the normal to the probe. This method offers the same performance as spatial coding and is described in document US 2003/0125628. There it is a question of synthesizing dynamic focusing on transmission by transmitting unfocused waves at different angles. That technique is close to the aperture synthesis method described above, with the difference that unfocused waves are transmitted instead of circular waves.

A number of methods have been developed in recent years, most often based on standard mode B imaging methods and aiming to augment the image acquisition rate.

Figure 5A:
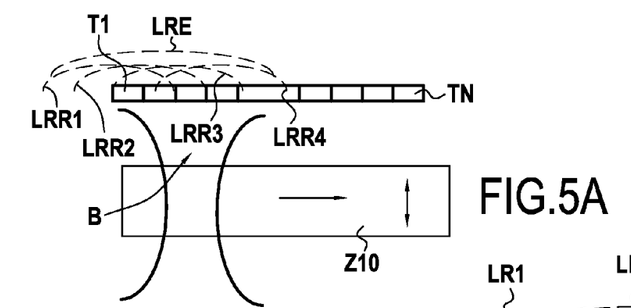
FIGS. 5A, 5B, and 5C show diagrammatically the operation of two methods of accelerating image acquisition by an echograph operating in multi-line mode, multi-beam mode, and unfocused wave mode.

The multi-line method, shown in FIG. 5A, consists in widening the transmission beam B using a particular transmission law LRE different from the particular reception laws LRR1 and LRR4 and adapted to enable the reconstruction of a plurality of $N_{line}$ lines in parallel (here four lines in parallel). The image acquisition rate is multiplied by $N_{line}$ but image quality in terms of resolution and contrast is degraded. This is described in the document by D. P. Shattuck et al. "Explososcan—a Parallel Processing Technique for High-Speed Ultrasound Imaging with Linear Phased-Arrays", Journal of the Acoustical Society of America, vol. 75, pp. 1273-1282, 1984. An optimum imaging area ZIO similar to that of the mode B method is obtained.

Figure 5B:
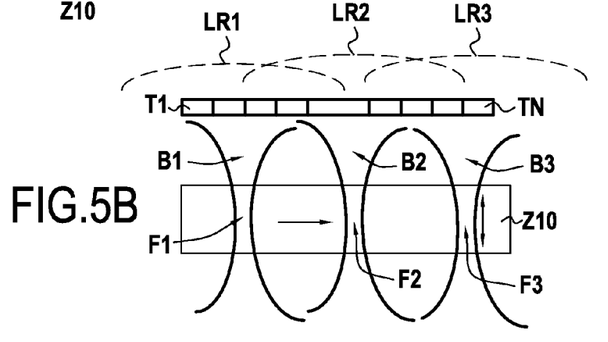

The multi-beam method shown in FIG. 5B consists in simultaneously transmitting a plurality of $N_{beam}$ beams B1 to B3 each focused at a point F1 to F3 using simultaneous transmission laws LR1 to LR3 and reconstructing a plurality of lines simultaneously. That method reduces the number of firings by a factor $N_{beam}$ but degrades image quality. That method is known from the thesis of J. Bercoff, "L'imagerie échographique ultrarapide et son application à l'étude de la viscoélasticité du corps humain" [Ultrafast echographic imaging and application to studying the viscoelasticity of the human body], Paris 7, 2004. The optimum imaging area ZIO obtained is similar to that obtained with the mode B method.

Figure 5C:
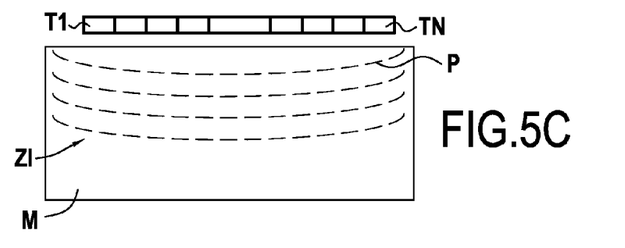

For its part, the unfocused wave mode, shown in FIG. 5C, consists in transmitting an unfocused wave OP and in reconstructing all of the lines of the imaged area ZI simultaneously. The unfocused wave may be a plane wave generated with no phase shifting applied to transmission by the various antenna elements T1 to TN. That method, which is optimum in image acquisition rate, exhibits strongly degraded image quality.

With the growth of 3D imaging systems, a so-called adaptive image acquisition rate imaging method has recently been developed. That method consists in taking into account the imaging context to adapt the image acquisition rate and consequently adapt image quality.

U.S. Pat. No. 6,346,079 discloses estimating the movement of the medium to be imaged and adjusting the number of firings accordingly. The movement is estimated by measuring the correlation of the brightness of successive images or by Doppler analysis of the acquired signals. The imaging method is of the mode B type. The number of firings necessary is varied by varying the aperture of the transmitted beams and thus reducing the number of imaged lines. Once again, the image acquisition rate is improved to the detriment of image quality.

As already seen, synthetic aperture methods furnish a set of complex so-called "low resolution" images. It is possible to weight the coherent summing in various ways as a function of what is required.

Thus spatial weighting may be effected. That consists in weighting the pixels of the low-resolution images as a function of the position of the pixel relative to the transmitter. If it is in the main transmission lobe, it is given a maximum weighting, whereas if it is outside that lobe its weighting is close to zero. That weighting enables the quality of the images to be greatly increased. Conventionally used cardinal sine, Tchebychev, or Hanning type weighting gives good results but the number of firings necessary is not reduced.

Weighting may also be effected by coherence measurement. Statistical measurements are then effected on the low-resolution sets of pixels, notably coherence measurements. Since anechoic areas are theoretically incoherent (white noise), weighting by the coherence map is going to lead to an increase in contrast. The idea is to use the coherence measurement of the same pixel between the so-called low-resolution images to improve the quality of the final so-called high-resolution image. That approach may be accentuated by weighting with the exponential of the coherence, but that leads to an increase in the sharpness of speckle. Finally, the use of a pre-adjusted error function enables contrast to be increased without degrading speckle. Nevertheless, it is again not possible to improve the image acquisition rate and that technique may be applied only to synthetic aperture systems.

The constant improvement in computation power and the increasing integration of programmable electronics of the field programmable gate array (FPGA) type are changing the nature of the problem of ultrasound imaging image acquisition rates. The image acquisition rate is less and less limited by the image reconstruction time but rather by the flight time of the beams or, in other words, the number of firings necessary to reconstruct the final image.

In parallel with this, the requirements for imaging with a high temporal resolution are of three kinds:
  Echography of the heart, where improving the temporal resolution would enable valve pathologies to be detected;
  Elastography, where it is necessary to visualize the propagation of shear waves in tissues with high temporal resolution;
  3D imaging, where standard focused transmission methods are unable to achieve high temporal resolutions.

Improving temporal resolution usually consists in widening the transmitted beams to enable the number of firings to be reduced. This reduction has the effect of degrading image quality in terms of resolution and contrast.

OBJECT AND SUMMARY OF THE INVENTION

The invention relates to an imaging method aiming to optimize the trade-off between image acquisition rate and image quality.

The present invention proposes a solution enabling reduction of the number of firings transmitted without loss of image quality. The invention relates to a device enabling improvement of the image acquisition rate compared to the techniques conventionally used but retaining optimum image quality. It also enables the image acquisition rate to be rendered adjustable as a function of the imaging context.

Thus the present invention has for its main objective to alleviate the drawbacks and limitations of the prior art devices and methods by proposing a method of acquiring high-resolution ultrasound images of a medium using an array of N transducers using successive transmission matrices, the method being characterized in that it comprises the steps of:

a) acquiring at least one preliminary image of the medium;
b) defining an area of interest in the preliminary image;
c) determining inter-transducer correlation matrices corresponding to the area of interest and to the unwanted area;
d) determining a characteristic matrix of the area of interest resulting from the product of the inverse of the inter-transducer correlation matrix of the unwanted area by the inter-transducer correlation matrix of the area of interest;
e) calculating eigenvectors and eigenvalues of the characteristic matrix of the area of interest, these vectors, classified as a function of their corresponding eigenvalues, defining a transmission matrix;
f) selecting the K eigenvectors associated with the K highest eigenvalues from the N eigenvectors;
g) firing K waves weighted by the selected K eigenvectors, each selected vector weighting the signals transmitted by the transducers during a firing, these vectors defining a truncated transmission matrix composed of, in a first part, the K vectors of the family of eigenvectors associated with the K highest eigenvalues of the characteristic matrix and, in a second part, columns of zeros corresponding to the firings that are not effected;
h) receiving the signals returned by the medium;
i) multiplying a reception matrix constituted of the acquired signals completed by data set to zero corresponding to the firings not effected by the inverse of the transmission matrix to obtain a complete data set;
j) extracting low-resolution images from the complete data set as in synthetic aperture echographic imaging methods; and
k) reconstructing the high-resolution image corresponding to the area of interest by coherent summing, as in synthetic aperture echographic imaging methods, of the low-resolution images extracted from the complete data set.

With the proposed method, it is possible to achieve a very high temporal resolution simply by reducing the size of the image.

Astutely and in a manner adaptable at will to a given particular area of interest, the invention moves away from the standard trade-off between image acquisition rate and image quality towards a trade-off between image acquisition rate and image size. The invention makes adjustment of the image acquisition rate possible simply by controlling the reduction of the size of the image obtained. The size of the high-resolution image obtained is then typically the size of the area of interest.

The method of the invention consists in transmitting an invertible transmission matrix having various vectors that generate beams enabling energy to be concentrated spatially. Each firing that is transmitted contributes to the reconstruction of a specific area, in such a manner that the suppression of this transmission law leads to a loss of the image of this area but does not degrade the quality of the other areas of the image to be reconstructed.

If, to accelerate image acquisition, some of the laws contained in the transmission matrix are not transmitted, $N_{suppr}$ vectors being suppressed in the truncated transmission matrix, the corresponding signals are assumed to be zero and the image acquisition rate is therefore increased by a factor $N_{el}/(N_{el}-N_{suppr})$, where $N_{el}$ is the number of transducers. The size of the image is reduced by the corresponding area, but image quality remains optimum.

Weighting consists, for each firing, in multiplying the signals transmitted by each of the sensors by each of the components of the eigenvector corresponding to the firing concerned.

The K waves fired during the step h) are advantageously unfocused.

This feature is entirely suited to use of the method of the invention, which introduces a spatial filter based on an invertible matrix. Nevertheless, it is noted here that a device using focused waves could equally benefit from the invention to increase the image acquisition rate. The invention may typically be used with arrays of pre-focused transducers, for example a curved transducer array.

In one implementation, for the characteristic matrix having I normalized eigenvalues meaningfully different from zero, K is equal to I.

The number I of normalized eigenvalues close to 1 is a function of the chosen area of interest. In this implementation, once the area of interest has been determined, the number K=I is defined and the reduced number of firings that define the increased image acquisition rate is then fixed automatically by that number. This choice of the number K may be a default choice provided in a device implementing the invention. If so, it should be observed that the number K is automatically modified by the device as a function of the area of interest and of the number of meaningfully non-zero eigenvalues of the characteristic matrix. The image quality obtained in the area of interest is then the optimum, whilst also obtaining an optimum image acquisition rate increase.

In another implementation, the method includes a step of adjusting a trade-off between image acquisition rate and image quality in the area of interest, the number K being a function of the adjustment of the trade-off between the image acquisition rate and image quality in the area of interest.

In this implementation, the number K may be less than the number I if a highly-increased image acquisition rate is required or if a lesser quality of the image defined during the adjustment step suffices.

The adjustment step may consist in adjusting a number K fixed independently of the number I. If so, the increase in the image acquisition rate is imposed and imposes a given image quality. The adjustment may also consist in an image quality requirement. It may be a question of automatic adjustments as a function of parameters external to the operation of the invention or adjustments offered directly to an operator.

In a preferred implementation, the transmission matrix is composed of prolate (flattened) spheroidal vectors.

This is a high-performance approach that optimizes the energy radiated in a cone. The transmission matrix is then composed of prolate spheroidal vectors (Slepian, D. (1978), "Prolate Spheroidal Wave Function, Fourier Analysis, and Uncertainty-V: The Discrete Case", *The Bell System Technical Journal*) with parameters $N_{el}$ and B. $N_{el}$ is the number of probe elements, $B=(dy_0)/(\lambda x_0)$, d is the distance between sensors, $\lambda$ is the wavelength of the acoustic pulse transmitted, and $x_0$ and $y_0$ define a cone of interest.

According to one particular feature, for the area of interest defined as being the complete image, the transmission matrix includes transmission laws corresponding to the prolate spheroidal vectors with a parameter B large enough to cover the complete image.

This feature authorizes reducing the number of firings by eliminating firings that correspond to vectors having eigenvalues significantly less than 1. The base of the prolate spheroidal vectors is the optimum in terms of the mean square error, i.e. it minimizes the loss of energy caused by truncating the base, this loss of energy exactly corresponding to the sum of the eigenvalues corresponding to the suppressed eigenvectors. It is for this reason that the eigenvectors retained are those that correspond to the highest eigenvalues and suppressing the other vectors does not compromise the acquisition of the complete image.

According to one particular feature of the invention, the high-resolution image is reconstructed from the complete data set for the area of interest defining an acquired area with a high image acquisition rate and high image quality, the rest of the image being a so-called background area reconstructed from a data set obtained at a lower image acquisition rate with different transmission laws.

The imaging area is then divided into two areas called the high image acquisition rate area and the background area. Two transmission laws are then chosen and specifically adapted to imaging each of the areas.

The transmission laws dedicated to the high image acquisition rate area are those of the invention. Since the high image acquisition rate area requires a smaller number of firings than the background area, it is imaged at a higher image acquisition rate than the background.

The step of reconstructing the high-resolution image on the principle of synthetic aperture imaging corresponding to the area of interest (D1) advantageously employs spatial weighting of the low-resolution images by coherence measurement.

The term "spatial weighting" means different weighting for each pixel, produced here for each coherence measurement. With such a feature, the image obtained has better contrast between echogenic areas and anechoic areas.

According to one particular feature, the method comprises a preliminary step of measuring movements in the preliminary image (ZI) and/or of the transducers (T1 to TN), the number of firings effected and thus the number of eigenvectors selected being modified as a function of the measured movements, thus modifying the image acquisition rate.

These movements may be detected and measured in various known ways, for example by correlating the successively acquired signals, by accelerometer and/or gyro measurement of the movements of the probe, or by correlating the brightnesses of the successive reconstructed images.

This obtains an image acquisition method with an automatically adaptive image acquisition rate. The step of measuring movements may also determine the area in which those movements are situated and thus define automatically an area of interest.

According to another particular feature, the method comprises a step of an operator selecting an area of interest.

This approach is of particular benefit for systems such as ultrasound cardiac imaging systems in which high temporal resolution is required over areas of small size.

The invention also provides a device for acquiring high-resolution ultrasound images of a medium, the device comprising an array of N transducers and a module for controlling the transducers using successive transmission matrices, and being characterized in that it further comprises:
  means for defining an area of interest in a previously-acquired image;
  means for determining inter-transducer correlation matrices corresponding to the area of interest and to the unwanted area;
  means for determining a matrix that is characteristic of the area of interest and that results from the product of the inverse of the inter-transducer correlation matrix of the unwanted area by the inter-transducer correlation matrix of the area of interest;
  means for calculating the eigenvectors and values of the characteristic matrix of the area of interest, these vectors, classified as a function of their corresponding eigenvalues, defining a transmission matrix;
  means for selecting K eigenvectors associated with the K highest eigenvalues;
  the control module being further adapted to fire K waves weighted by the selected K eigenvectors, each selected vector weighting the signals transmitted by the transducers during a firing, these vectors defining a truncated transmission matrix composed of, in a first part, the K vectors of the family of eigenvectors associated with the K highest eigenvalues of the characteristic matrix and, in a second part, columns of zeros corresponding to the firings that are not effected;
  means for receiving the signals returned by the medium;
  means for taking the acquired signals, together with data that is set to zero and that corresponds to the firings not effected in order to make up a receiving matrix, and multiplying by the inverse of the transmission matrix in order to obtain a complete data set;
  means for extracting low-resolution images from the complete data set as in synthetic aperture echographic imaging methods; and
  means for reconstructing the high-resolution image corresponding to the area of interest (D1) by coherent summing, as in synthetic aperture echographic imaging methods, of the low-resolution images extracted from the complete data set.

In a preferred embodiment, the various steps of the method of the invention are determined by computer program instructions.

Consequently, the invention also provides a computer program on an information medium, the program being adapted to be executed in a computer and including instructions adapted to execute the steps of the method of the invention.

The program may use any programming language and take the form of source code, object code, or a code intermediate between source code and object code, such as a partially-compiled form, or any other desirable form.

The invention also provides a computer-readable information medium containing instructions of a computer program as referred to above.

The information medium may be any entity or device capable of storing the program. For example, the medium may include storage means, such as a read-only memory (ROM), for example a CD ROM or a micro-electronic circuit ROM, or magnetic storage means, for example a floppy disk, a hard disk, a flash memory, a universal serial bus (USB) key, etc.

In contrast, the information medium may be a transmissible medium such as an electrical or optical signal, which may be routed via an electrical or optical cable, by radio, or by other means. The program of the invention may in particular be downloaded over an Internet-type network.

Alternatively, the information medium may be an integrated circuit in which the program is incorporated, the circuit being adapted to execute the method in question or to be used in its execution.

BRIEF DESCRIPTION OF THE DRAWINGS

Other features and advantages of the present invention emerge from the description given below with reference to the appended drawings, which show one non-limiting implementation of the present invention. In the figures.

DETAILED DESCRIPTION OF ONE IMPLEMENTATION

Figure 6:
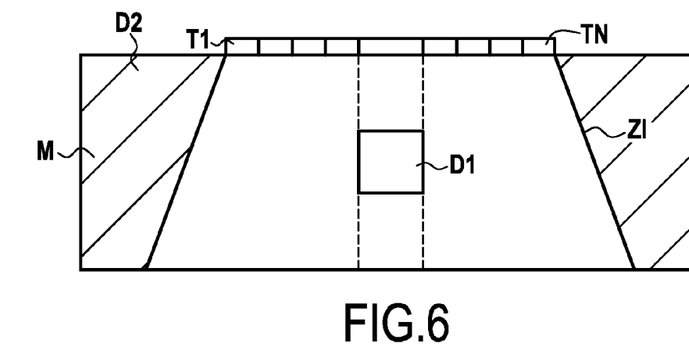
FIG. 6 shows diagrammatically an area imaged beforehand and the determination of an area of interest ZINT.

FIG. 6 shows diagrammatically the outcome of the first step of the method, that of acquiring an imaged area ZI of the medium M to be imaged from which an area of interest D1 is determined.

This area of interest D1 may be determined automatically in the device using the method of the invention by analyzing the image or the successive images when it is a question of imaging moving structures.

The area of interest D1 may also be determined manually by an operator selecting an area within the image area following display of the image area.

The method of the invention then comprises the step of determining inter-transducer correlation matrices corresponding to the area of interest and the unwanted area.

To this end, the method of the invention considers an array of acoustic transducers T1 to TN of dimension N, an echographic probe, for example, and a region of interest D, an area in space that it is required to image.

$X(t)=[x_1(t), x_2(t), \ldots, x_N(t)]^\tau$ denotes the vector composed of the signals acquired by each of the transducers of the probe at time t.

Of interest are the signals that would be received by the probe if an infinite number of infinitesimal sources were to transmit a wave. In the general case, $R(\tau)$ is the correlation matrix of $X(t)$ and is defined as follows: $R(\tau)=E\{X(t)X^*(t-\tau)\}$.

$E\{\cdot\}$ represents the mathematical expectation operator and * represents the conjugate and transposed operator.

The elements of the matrix $R(\tau)$ are constituted of cross correlation terms of the signals acquired at each of the transducers: $R_{kl}(\tau)=E\{x_k(t)x_l^*(t-\tau)\}$.

In the very special case of the invention, of interest are the inter-transducer correlation matrices obtained with an infinite number of infinitesimal monochromatic sources distributed in a particular area D. The variations of $R_{kl}(\tau)$ as a function of the parameter $\tau$ then depend on the geometry of the particular area chosen.

For the requirements of the invention, time dependency is eliminated by integration relative to T, the aim being to calculate the energy at the output of the spatial filter. There is determined in this way an instantaneous inter-transducer correlation matrix $J_{kl}$ that is not dependent on the times t and T and that is adapted to the geometry of the area D and to the array of transducers:

$$J_{kl}(D) \triangleq \int_D E\{x_k(t)x_l^*(t-\tau_{kl}(D))\} d\tau_{kl}(D) \quad (1)$$

Note that $J_{kl}(D)=E\{x_k(t)x_l^*(t)\}$, i.e. $J(D)=E\{X(t)X^*(t)\}$.

A spatial filter is constituted of a battery of regular linear and invariant filters, i.e. the output of each of these filters is obtained from the convolution product of the input signal of the filter and the impulse response of the filter.

The convolution product is defined as follows:

$$v(t) = \int_{-\infty}^{+\infty} u(\theta)h(t-\theta)d\theta, \quad (2)$$

where $v(t)$ is the output signal, $u(t)$ the input signal, and $h(t)$ the impulse response of the filter.

A spatial filter on N transducers is constituted of N vectors $h_k$ of dimension M defining the length of the filters. The spatial filter is written H. Its response to a signal vector acquired at the transducers X is as follows:

$$y(t) = \sum_{k=1}^{N} h_k(t) * x_k(t). \quad (3)$$

In the general case, a space-time filter has two dimensions: a space dimension (dimension of the sensors), and a time dimension. The invention relates to the very special case for which the length of the filters M is equal to 1 because $h_k(t)$ does not depend on time and becomes $h_k$. An intentional limitation to a purely spatial filter is obtained by weighting the transducers with a law that does not depend on time. Then $H = [h_1, h_2, \ldots, h_N]^\tau$.

The convolution product of equation (3) then becomes a product between scalars, and the response at the output of the spatial filter becomes:

$$y(t) = \sum_{k=1}^{N} h_k \cdot x_k(t) = H * X(t) \quad (4)$$

The energy of the signal at the output of the filter is, by definition:

$$\delta \triangleq E\{y^2(t)\} \quad (5)$$

By injecting equation (4) into equation (5) there is obtained:

$$\delta = E\{H*X(t)X*(t)H\} = H*E\{X(t)X*(t)\}H = H*J(D)H \quad (6)$$

The filter H is then searched for, which is a vector or a weighting or apodization law that maximizes the ratio ρ of the energies $\delta_1$ and $\delta_2$ corresponding to two areas D1 and D2, D1 being the area of interest and D2 the unwanted area (deemed of no utility) of the rest of the half-space in front of the probe. To this end, the gradient of ρ, denoted ∂ρ, is cancelled out.

$$\rho(H) = \frac{H*J(D_1)H}{H*J(D_2)H} \quad (7)$$

$$\partial \rho = 2 \frac{J(D_1)H - \rho J(D_2)H}{H*J(D_2)H} \quad (8)$$

By canceling out ∂ρ, there is obtained:

$$J(D_2)^{-1}J(D_1)H = \rho H \quad (9)$$

In other words, the filter $H_{Opt}$ that maximizes the ratio of the energies $\delta_1$ and $\delta_2$ is the eigenvector of the matrix $MC = J(D_2)^{-1}J(D_1)$, called the characteristic matrix of the area of interest, associated with its greatest eigenvalue $\mu_0$. Moreover, the energy at the output of the filter is then equal to the eigenvalue that is associated with it: $\rho = \mu_k$ at the output of the filter $H_k$. The invention thus comprises, for each defined area of interest, a step of determining a so-called characteristic matrix of the area of interest resulting from the product of the inverse of the inter-transducer correlation matrix of the unwanted area by the inter-transducer correlation matrix of the area of interest.

The major idea of the invention consists in constructing the sequence of imaging firings with weighting laws on the transducers corresponding to the eigenvectors of the characteristic matrix of the area of interest $MC = J(D_2)^{-1}J(D_1)$ linked to the highest eigenvalues.

The method of the invention thus comprises the step of calculating the eigenvectors and eigenvalues of the characteristic matrix of the area of interest. These vectors, classified as a function of their corresponding eigenvalues, define a transmission matrix. To be more precise, these eigenvectors are going to constitute the first K columns of the transmission matrix, and the other components of this matrix are set to zero, signifying that no firing is effected, which enables an increase in the image acquisition rate. By construction, the matrix constituted by the vectors $H_k$ is invertible. Note however that it is not necessarily orthogonal.

This method enables N−K firings to be dispensed with and thus the image acquisition rate to be increased in a ratio $$\frac{N}{N-K}.$$

The loss of energy σ in the area of interest is perfectly quantified and has the value:

$$\sigma = \sum_{k=K+1}^{N} \mu_k \quad (10)$$

Figure 7:
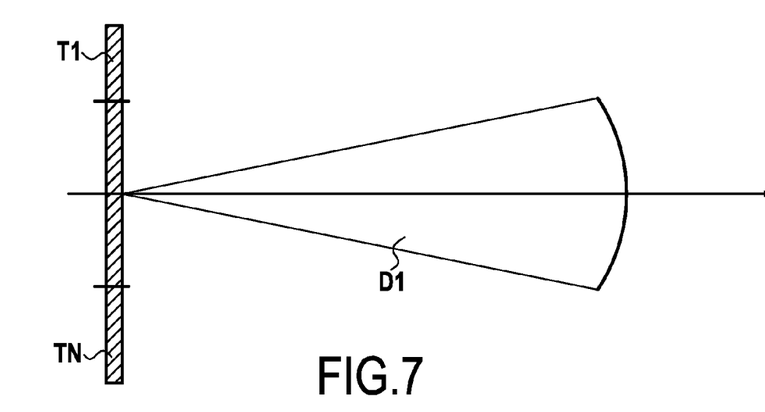
FIG. 7 shows an example of a far-field area of interest.

FIG. 7 shows an area of interest D1 that is particularly advantageous. An example is given for a linear probe with this kind of definition of the area of interest D1.

Here the region of interest D1 is defined by a circular arc placed in theory at an infinite distance from the probe (far field) and by an angle Φ. The unwanted area D2 corresponds to the rest of the half-space in front of the probe.

Under such circumstances, it can be shown that:

$$MC = J_{kl}(D_2)^{-1}J_{kl}(D_1) = \frac{\sin[2\pi(l-k)B]}{\pi(l-k)} \quad (11)$$

where $$B = \frac{d\sin\phi}{\lambda}, \quad \lambda = \frac{c}{f},$$

d is the inter-transducer distance, f is the center frequency of the wave, and c is the speed of sound in the medium.

The elements $P_{kl}$ of the matrix P with dimensions N×N are defined by $P_{kl} = \sin[2\pi(l-k)B]/[\pi(l-k)]$.

The eigenvectors of the matrix P define the prolate spheroidal sequence of order N and of bandwidth B that is described in Slepian, D. (1978), "Prolate Spheroidal Wave Function, Fourier Analysis, and Uncertainty—V: The Discrete Case", The Bell System Technical Journal. Here, N is the number of transducers of the probe. This sequence is a fairly standard signal processing tool, especially in spectral analysis. The equations (9) and (11) show that the prolate spheroidal vectors maximize the ratio of the energy transmitted in the sector [−Φ; Φ] relative to the energy radiated in the half-space in front of the probe without the sector [−Φ; Φ]. It has been shown in Forster, P. & Vezzosi, G. (1987), "Application of Spheroidal Sequences to Array Processing", Proceedings IEEE International Conference on Acoustics, Speech and Signal Processing, that only the 2BN−2 highest eigenvalues of the prolate spheroidal bases, and thus of the matrix MC defined by equation (11), are meaningful, i.e. the others are very close to zero, and the eigenvectors that are associated with them contribute only negligible energy in the sector $[-\Phi; \Phi]$. In other words 2BN-2 firings are sufficient for an optimum image.

It has been shown that the prolate spheroidal vectors furnish an optimum solution for far-field imaging in an angular sector.

In contrast, ultrasound medical imaging systems do not produce far-field images but near-field images. Thus the invention proposes to use the spheroidal bases, the optimum for far-field imaging, for echographic imaging, i.e. for near-field imaging. To what approximation and under what conditions the spheroidal sequences address the near-field problem is explained.

Figure 8:
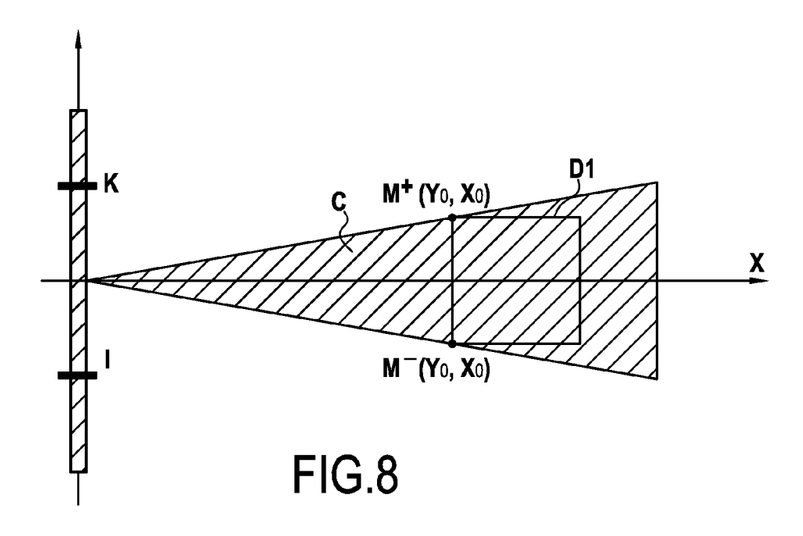
FIG. 8 shows an example of a near-field area of interest.

FIG. 8 shows a near-field area of interest D1 and the definition of a cone of interest C in which the near-field approximations of the spheroidal bases are to be studied.

The situation considered here is that of an area D1 constituting a rectangle situated behind a segment $[M^+, M^-]$ situated at a distance $x_0$ from the probe. In this case, it can be shown that the characteristic matrix MC has the following expression:

$$MC_{kl} = e^{-2i\pi \frac{d^2(l-k)(l+k)}{2x_0 c}} \frac{\sin[2\pi(l-k)B]}{\pi(l-k)} \quad (12)$$

in which $$B = \frac{dy_0}{\lambda x_0} \quad (13)$$

MC is then a complex matrix. Equation (12) represents MC in its form of the product of its modulus by a complex exponential of type $MC_{kl} = re^{i\Phi}$. The terms of MC are thus entirely defined by their modulus and their phase term $\phi$.

At the orders of magnitude of ultrasound echography, the phase term $\phi$ is very close to zero. For example, for a probe with 192 elements, center frequency 5 MHz, inter-sensor distance 0.3 mm, and a segment $[M^+, M^-]$ placed at a distance of at least 5 mm, then the phase $\phi$ of the equation (12) is still negligible:

$$\varphi = \frac{d^2(k-l)(k+l)}{2x_0 c} \leq 2.16 \cdot 10^{-4}$$

The following approximation is therefore perfectly valid for medical ultrasound imaging:

$$MC_{kl} \approx \frac{\sin[2\pi(l-k)B]}{\pi(l-k)} \quad (14)$$

Equation (14) shows that the spheroidal bases constitute a more than adequate approximation of the optimum vectors for an area of interest constituting a segment placed in the near field. The parameter B of the spheroidal functions then depends on the ratio between the length of the segment and its distance from the antenna. Equation (13) shows clearly that the characteristic matrix MC remains constant if the ratio $y_0/x_0$ remains constant; in other words, the area of interest constitutes a cone in front of the probe. The aperture of this cone depends on the ratio $y_0/x_0$. This cone is defined in equivalent manner by the angle $\Phi = \arctan(y_0/x_0)$.

For a particular example, the method of the invention therefore determines this matrix MC and calculates the associated eigenvalues for an angle $\Phi$ of approximately 23°, a probe with 128 elements that have an inter-transducer distance of 0.3 mm, a center frequency of 5 MHz, and a speed of sound of 1540 m/s.

Figure 9:
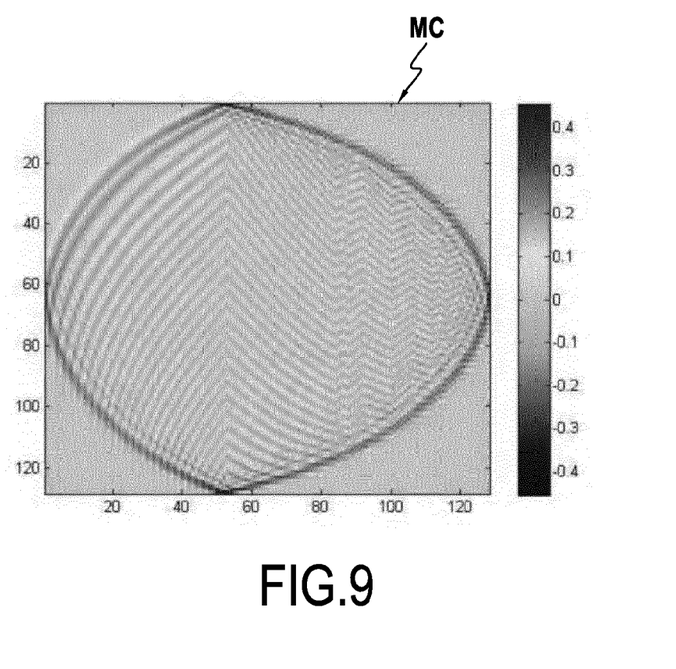
FIG. 9 shows a first example of a spheroidal matrix characteristic of the particular area of interest shown in FIGS. 7 and 8.
Figure 10:
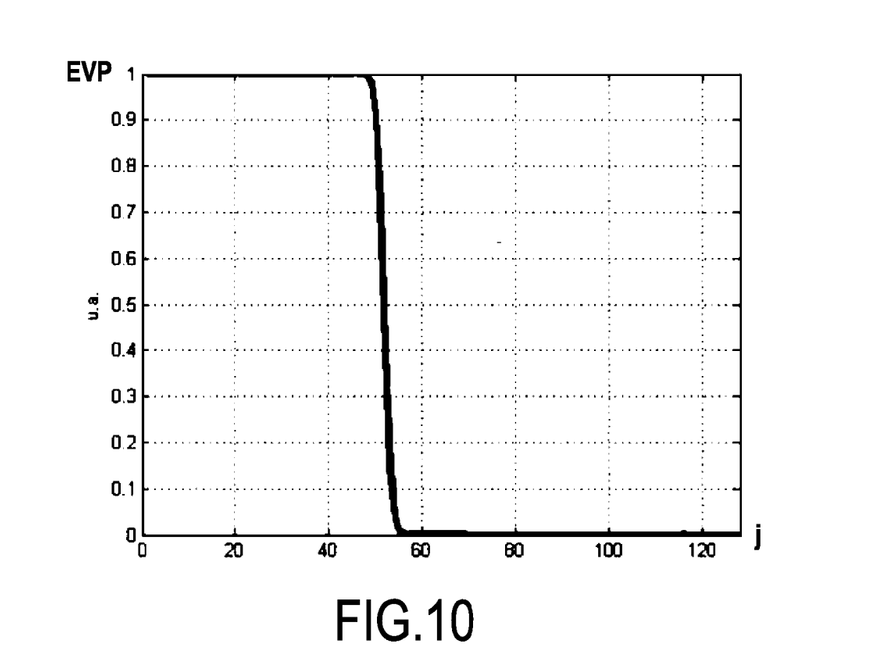
FIG. 10 shows the eigenvalues as a function of their index for the matrix from FIGS. 7 and 8.
Figure 11A:
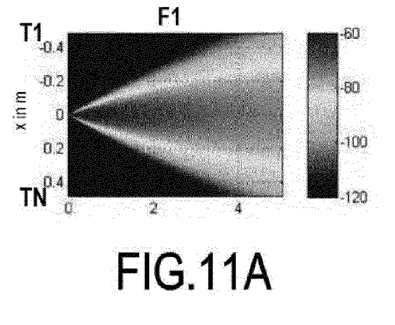
FIG. 11A to 11D show four flattened spheroidal beams.
Figure 11B:
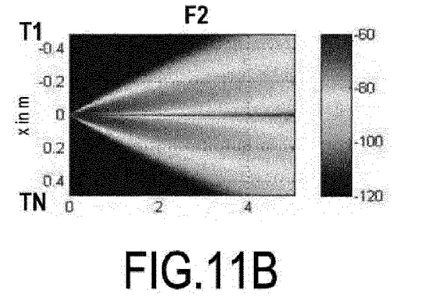
Figure 11C:
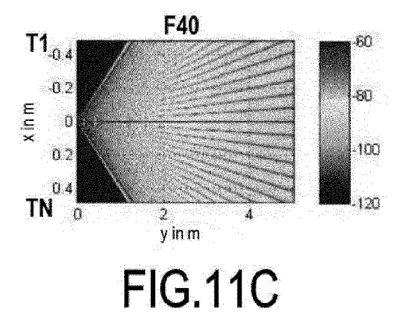
Figure 11D:
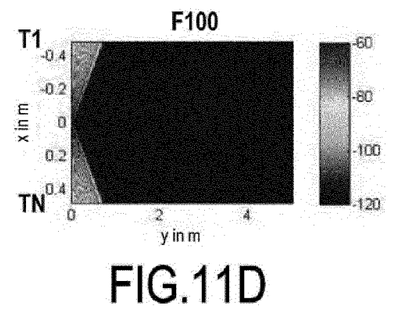

FIG. 9 is a two-dimensional representation of a characteristic matrix MC in which the intensities of the elements (i, j) are represented by a color code. FIG. 10 shows an energy criterion of the eigenvalues EVP as a function of their index j for the FIG. 8 matrix.

It is seen that the eigenvalues having a rank greater than 50 have values that are virtually zero, the energy $\delta$ radiated by the corresponding eigenvectors in the sector $[-23°; 23°]$ is therefore also zero.

The eigenvectors associated with the non-negligible eigenvalues are generally then selected. By non-negligible eigenvalues is meant eigenvalues close to 1.

As may be seen in FIG. 10, even for relatively wide sectors of interest, exceeding 2×60°, the number of quasi-zero eigenvalues remains high.

The eigenvectors corresponding to the negligible eigenvalues are not fired, thus enabling the image acquisition rate to be increased.

Since the energy radiated by these vectors in the sector of interest corresponds to their eigenvalues, this energy is also quasi-zero. Thus not using these vectors does not change in any way the final image since they do not contribute to sounding the imaged area.

Reducing the number of firings while retaining the complete image size may even be envisaged. The spheroidal bases enable an image of sufficient quality to be obtained by reducing the number of firings, including in near-field imaging.

Using the FIELD II software described in Jensen, J. A. (1996), "Field: A program for simulating ultrasound systems", 10th Nordic-Baltic Conference on Biomedical Imaging, pp. 351-353, Vol. 34, Supplement 1, Part 1, the transmitted beams F1, F2, F40, and F100 have been simulated using the 1st, 2nd, 40th and 100th spheroidal vectors. The spatial distributions of the transmitted acoustic intensity are shown in FIGS. 11A to 11D, respectively.

The first beams, i.e. those associated with the highest eigenvalues, send energy only in the sector of interest, while the last, associated with the quasi-zero eigenvalues, send energy only outside the area of interest.

Effecting the firings corresponding to the quasi-zero eigenvalues and performing the corresponding acquisition does not enhance the image because these firings send energy outside the area of interest. For example, it should be observed in FIG. 11D that the transmission effected is of no benefit for the area to be imaged.

In this example, the improvement in image acquisition rate is 1.78 without modifying the quality of the image in the area of interest D1. The image acquisition rate increase could of course be greater if the number of eigenvectors were reduced, but at the cost of lower image quality.

It is important to note that the number of eigenvectors necessary for optimum image quality is a function of the size of the region of interest D1. In this example this means the size of the angular sector.

Figure 12:
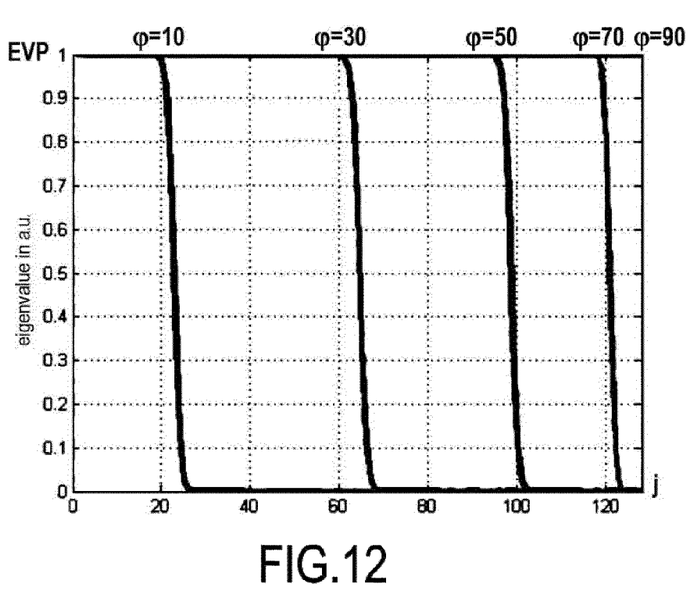
FIG. 12 shows the evolution of the set of eigenvalues with the size of the angular sector defining the area of interest.

FIG. 12 shows the sets of eigenvalues of MC for an energy criterion EVP as a function of their index j for values of $\phi$ in the range 10° to 70° using the same parameters as before, same frequency, etc.

It is thus apparent that the number of zero eigenvalues decreases as the size of the sector increases.

It should be noted that spheroidal bases constitute a special case and the general method consists in maximizing the ratio of the energy in the area of interest to the energy in the unwanted area by taking the first eigenvectors of the matrix MC that correspond to the area of interest D1, to the area D2, and to the geometry of the probe.

Moreover, the example given here relates to two-dimensional imaging, but the method also applies to three-dimensional imaging.

Figure 13:
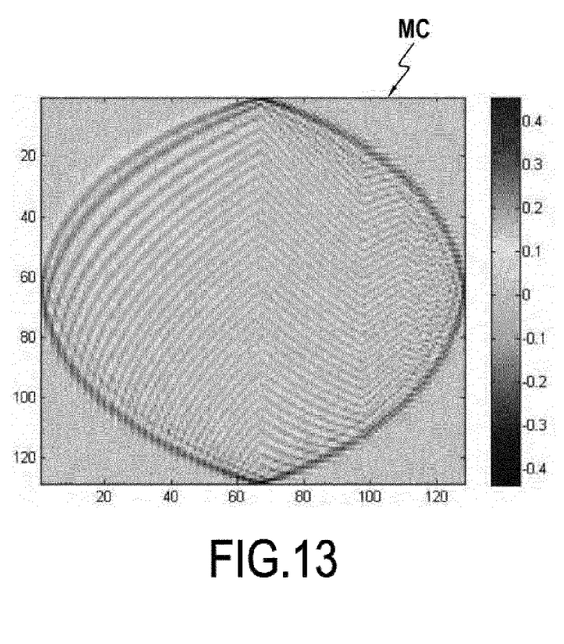
FIG. 13 shows a spheroidal matrix characteristic of an area of interest with an angular aperture of 60° determined during the method of the invention.
Figure 14:
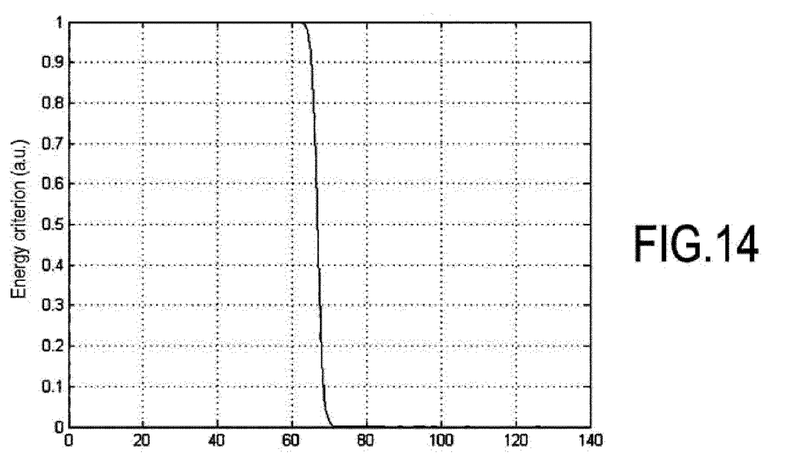
FIG. 14 shows the eigenvalues as a function of their index for the matrix from FIG. 13.
Figure 15A:
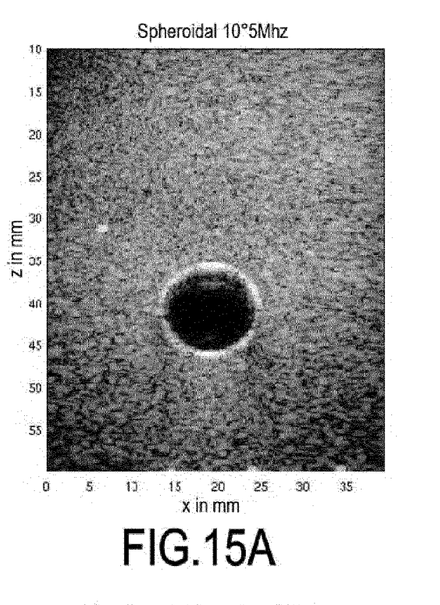
FIGS. 15A to 15D show, in negative, the results obtained for the first 4, 10, 20 firings and for all of the firings, respectively, of the spheroidal matrix from FIG. 13.
Figure 15B:
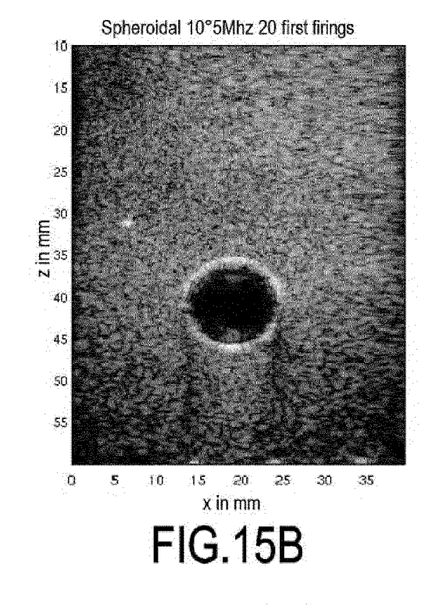
Figure 15C:
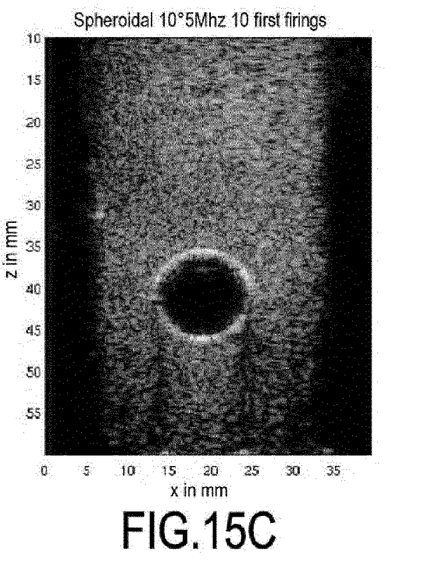
Figure 15D:
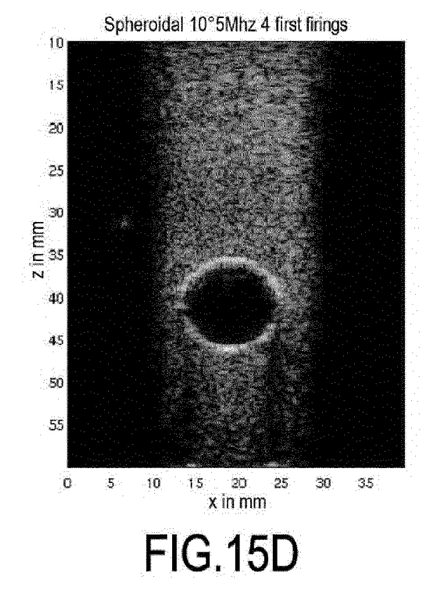

FIG. 13 shows a second example of a characteristic matrix MC for an area of interest with an angular aperture of 60°. FIG. 14 shows the associated eigenvalues. It is seen that a greater number of firings must be effected for a similar result from the point of view of image quality. An application example has been used to evaluate the performance of the method of the invention.

The probe used is a linear probe with $N_{el}$=128 elements functioning at 5 MHz. The aperture of the probe elements is 30°. The spheroidal matrix adopted is the FIG. 13 matrix, of size 128 and with the parameter B defined as follows:

$$B = \frac{d\sin\varphi_b}{\lambda}$$

where d is the inter-sensor distance 0.3 mm, $\lambda$ is the wavelength of 0.3 mm, and $\phi_b$ is the aperture half-angle of the area of interest, here 15°.

Here B=0.259. The parameters B and $N_{el}$ suffice to dimension the flattened spheroidal matrix. The number of non-redundant firings, i.e. firings corresponding to the number of meaningful eigenvalues, for such a configuration is given by the equation:

$N_{sph}=2N_{el}B-2$

Here $N_{sph}$=64.

Note here that the method therefore enables imaging of the whole of the area of interest with an optimum quality for half the number of firings compared to the mode B method, which is optimum only around the focal distance.

Each of the $N_{sph}$ firings is transmitted into the medium, i.e. the same temporal burst is applied to the various elements but weighted on the $i^{th}$ firing of the sequence by the $i^{th}$ column vector of the transmission matrix, constituted for a first part by the eigenvectors of the characteristic matrix of the area of interest shown in FIG. 13 and for a second part of zero vectors.

Each acquisition is stored in a 3D signal matrix in which the rows are the temporal samples, the columns are the sensors, and the depths are the firings, so that $C_{ijk}$ corresponds to the sample acquired at the time $i*F_e$, where $F_e$ is the sampling frequency of the system at the $j^{th}$ sensor for the $k^{th}$ acquisition.

At the end of the acquisition process, the signal matrix is then a matrix/tensor of dimension $N_{sample}*N_{el}*N_{sph}$. It is concatenated with the zero matrix of dimension $N_{sample}*N_{el}*(N_{el}-N_{sph})$ to form the complete signal matrix of dimension $N_{sample}*N_{el}*N_{el}$. The complete data set is then reconstructed. For this, each slice, corresponding to a given time, constituting a matrix of dimension $N_{el}*N_{el}$ is then leftward multiplied by the inverse of the transmission matrix, which is constant in time, in order to reconstruct the complete data set.

Each slice of the complete data set in the capture/time plane is then reconstructed by application of the corresponding delay laws to form one of the $N_{el}$ "low resolution" images. These are then summed coherently to obtain the high-resolution image.

Note that each acquisition provides information on only a limited area of the image. The $N_{sph}$ usable spheroidal vectors have precisely the property of having orthogonal spatial spectra. They are furthermore ordered spatially. The vector $N_i$ provides information on the angular sectors $[\theta_i, \kappa_{i+1}]$ and $-[\theta_{i+1}, -\theta_i]$ for the far field. For the near field it provides information on the widths $[X_i, X_{i+1}]$ and $[-X_{i+1}, -X_i]$. The transmission of the first $N_i$ vectors $(N_i<N_{sph})$ leads to a reduction in the size of the image and a further improvement in the image acquisition rate $N_{sph}/N_i$. It is thus seen that the image acquisition rate is variable.

The invention enables the image acquisition rate to be adjusted by a simple command to reduce the size of the image obtained and thus by simple definition of an area of interest size. This adjustment of the image acquisition rate may be effected manually by the operator or automatically by a movement detection and image acquisition rate adjustment algorithm.

FIGS. 15A to 15D show, in negative, the results obtained for the first 4, 10, 20 firings and for all of the firings of the FIG. 13 spheroidal matrix, respectively. It is seen that provided that the point target is centered in the imaged area, the resolution is virtually not degraded. The signal-to-clutter ratio, which corresponds to the quality of the contrast in the anechoic areas, does not vary either. Only the size of the image is reduced.

The table below sets out experimental results obtained from in vitro experiments.

|  | Sph_Full | Sph_60 | Sph_30 | Sph_20 | Sph_10 | Sph_4 |
| --- | --- | --- | --- | --- | --- | --- |
| Lateral resolution | 1.62 mm | 1.62 mm | 1.68 mm | 2.02 | / | / |
| Axial resolution | 0.65 mm | 0.66 mm | 0.67 mm | 0.74 | / | / |
| Number of firings | 128 | 60 | 30 | 20 | 10 | 4 |
| CTR in dB | −29.5 | −29.5 | −28.3 | −27.5 | −27.4 | −28.4 |
| Width of imaged area | 40 mm | 40 mm | 40 mm | 40 mm | 30 mm | 20 mm |

With the invention, in contrast to mode B, the quality of the image is constant for all depths.

Figure 16A:
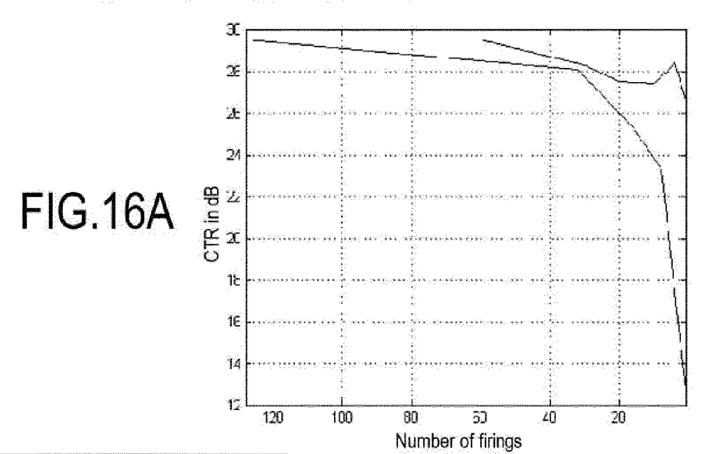
FIGS. 16A and 16B show the performance of the method of the invention obtained by applying the matrix from FIG. 13.

FIG. 16A shows the contrast C as a function of the lightening in terms of the number of firings AT (inverted abscissa axis) for the application of two types of matrix: Hadamard matrices used for spatial coding and characteristic matrices of an area of interest as determined in accordance with the invention. It is seen that, even for a very low number of firings, the invention enables very good contrast to be obtained.

Figure 16B:
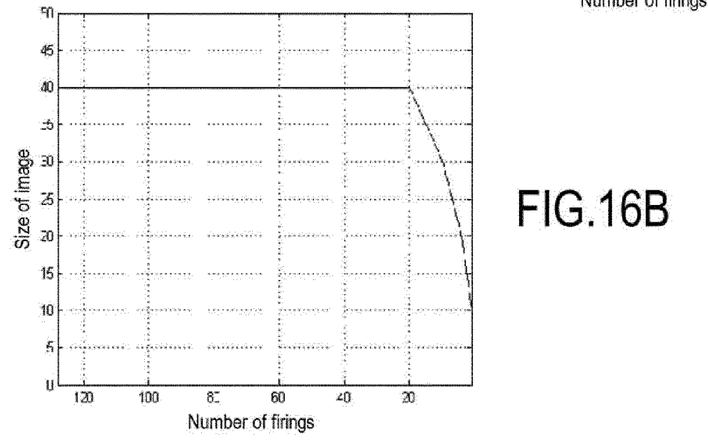

FIG. 16B shows the variation of the size of the image as a function of the number of firings obtained with the invention. It is seen that the size of the image achieves its optimum level from 20 firings.

It is possible to use the method of the invention to acquire an entire imaged area over which an area of interest is obtained that is imaged with high quality and an area external to the area of interest is obtained that is imaged with low quality.

Figure 17:
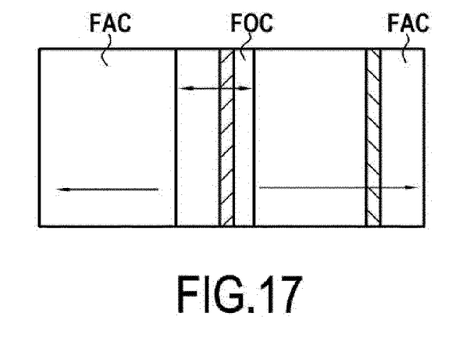
FIG. 17 shows diagrammatically the operation of the multi-image acquisition rate mode of the invention.

In one particular implementation, effecting multi-image acquisition rate acquisitions is also envisaged. Thus as shown in FIG. 17, the imaging area is then divided into two areas, the first called the high image acquisition rate area FOC and the second called the background area FAC. Two transmission laws are then chosen and specifically adapted to imaging each of the areas. For example a first transmission law is then activated every 10 images and is used to acquire the entire imaging area, and the next 9 images are acquired with the transmission laws of the invention.

Another implementation consists in effecting acquisitions with high image acquisition rate for the two areas, but with different image qualities, by giving preference to the area of interest. The area of interest is sounded in accordance with the principle of the present invention, the remainder of the image being sounded in accordance with the principles of high image acquisition rate with degraded image quality. The high image acquisition rate and degraded image quality transmission laws may be: imaging using unfocused waves as shown in FIG. 5C, multi-beam imaging as shown in FIG. 5B, multi-line imaging as shown in FIG. 5A, or synthetic aperture imaging with depointed plane waves as described in document US 2003/0125628. The number of unfocused waves transmitted is then relatively small to satisfy the high-image acquisition rate criterion, which is possible only to the detriment of image quality. Two transmission sequences alternate: acquisition of the area of interest with the transmission laws of the invention, and acquisition of the remainder of the image with transmission laws corresponding to the high-image acquisition rate mode with low-image quality.

Note finally that various implementations may be arrived at conforming to the principles of the invention.

The invention claimed is:

1. A method of acquiring high-resolution ultrasound images of a medium using an array of N transducers using successive transmission matrices, the method comprising the steps of:
   a) acquiring at least one preliminary image of the medium;
   b) defining an area of interest in the preliminary image;
   c) determining inter-transducer correlation matrices, including an inter-transducer correlation matrix corresponding to the area of interest and an inter-transducer correlation matrix corresponding to an unwanted area;
   d) determining a characteristic matrix of the area of interest resulting from a product of an inverse of the inter-transducer correlation matrix corresponding to the unwanted area by the inter-transducer correlation matrix corresponding to the area of interest;
   e) calculating eigenvectors and eigenvalues of the characteristic matrix of the area of interest, these eigenvectors, classified as a function of their corresponding eigenvalues, defining a transmission matrix;
   f) selecting K eigenvectors associated with K highest eigenvalues from N eigenvectors;
   g) firing K waves weighted by the selected K eigenvectors, each of the selected eigenvector weighting the signals transmitted by the transducers during a firing, these eigenvectors defining a truncated transmission matrix composed of, in a first part, the K vectors of the family of eigenvectors associated with the K highest eigenvalues of the characteristic matrix and, in a second part, columns of zeros corresponding to the firings that are not effected;
   h) receiving the signals returned by the medium;
   i) multiplying a reception matrix constituted of the acquired signals completed by data set to zero corresponding to the firings not effected by the inverse of the transmission matrix to obtain a complete data set;
   j) extracting low-resolution images from the complete data set as in synthetic aperture echographic imaging methods; and
   k) reconstructing the high-resolution image corresponding to the area of interest by coherent summing, as in synthetic aperture echographic imaging methods, of the low-resolution images extracted from the complete data set.

2. A method according to claim 1, wherein the K waves fired during step g) are unfocused.

3. A method according to claim 1, wherein for the characteristic matrix having I eigenvalues meaningfully different from zero, the K is equal to I.

4. A method according to claim 1 further comprising adjusting an image acquisition rate/image quality trade-off in the area of interest, the number K being a function of the adjustment of the image acquisition rate/image quality trade-off in the area of interest.

5. A method according to claim 1, characterized in that the transmission matrix is composed of prolate spheroidal vectors.

6. A method according to claim 5, wherein, for the area of interest defined as being the complete image, the transmission matrix includes transmission laws corresponding to K prolate spheroidal vectors that are sufficiently large to cover the complete image.

7. A method according to claim 1, wherein the high-resolution image is reconstructed from the complete data set for the area of interest defining an area acquired with a high image acquisition rate and high image quality, the remainder of the image being a so-called background area reconstructed from a data set obtained at a lower image acquisition rate with different transmission laws.

8. A method according to claim 1, wherein the step of reconstructing the high-resolution image corresponding to the area of interest by coherent summing of the low-resolution images employs spatial weighting by coherence measurement.

9. A method according to claim 1, further comprising measuring movements in the preliminary image and/or of the transducers, the number of firings effected and thus the number of eigenvectors selected being modified as a function of the measured movements, thus modifying the acquisition image acquisition rate.

10. A method according to claim 1, further comprising an operator selecting an area of interest.

11. The method of claim 1, further comprising a computer-readable recording medium storing a computer-executable program including instructions for executing the steps of the method according to claim 1.

12. A device for acquiring high-resolution ultrasound images of a medium, the device comprising an array of N transducers and a control module for controlling the transducers using successive transmission matrices, and being characterized in that it further comprises:
    means for defining an area of interest in a previously-acquired image;
    means for determining inter-transducer correlation matrices, including an inter-transducer correlation matrix corresponding to the area of interest and an inter-transducer correlation matrix corresponding to an unwanted area;

means for determining a matrix characteristic of the area of interest and that results from a product of an inverse of the inter-transducer correlation matrix corresponding to the unwanted area by the inter-transducer correlation matrix corresponding to the area of interest;

means for calculating eigenvectors and values of the characteristic matrix of the area of interest, these eigenvectors, classified as a function of their corresponding eigenvalues, defining a transmission matrix;

means for selecting K eigenvectors associated with K highest eigenvalues, the control module being further adapted to fire K waves weighted by the K eigenvectors that were selected, each selected eigenvector weighting the signals transmitted by the transducers during a firing, these eigenvectors defining a truncated transmission matrix composed of, in a first part, the K vectors of the family of eigenvectors associated with the K highest eigenvalues of the characteristic matrix and, in a second part, columns of zeros corresponding to the firings that are not effected;

means for receiving the signals returned by the medium;

means for taking the acquired signals, together with data that is set to zero and that corresponds to the firings not effected in order to constitute a receiving matrix, and multiplying by the inverse of the transmission matrix in order to obtain a complete data set;

means for extracting low-resolution images from the complete data set as in synthetic aperture echographic imaging methods; and means for reconstructing the high-resolution image corresponding to the area of interest by coherent summing, as in synthetic aperture echographic imaging methods, of the low-resolution images extracted from the complete data set.

13. A computer-readable storage medium on which is stored a computer program including instructions that when executed by a computer perform a method of acquiring high-resolution ultrasound images of a medium using an array of N transducers using successive transmission matrices, the method comprising:

acquiring at least one preliminary image of the medium;

defining an area of interest in the preliminary image;

determining inter-transducer correlation matrices, including an inter-transducer correlation matrix corresponding to the area of interest and an inter-transducer correlation matrix corresponding to an unwanted area;

determining a characteristic matrix of the area of interest resulting from a product of an inverse of the inter-transducer correlation matrix corresponding to the unwanted area by the inter-transducer correlation matrix corresponding to the area of interest;

calculating eigenvectors and eigenvalues of the characteristic matrix of the area of interest, these eigenvectors, classified as a function of their corresponding eigenvalues, defining a transmission matrix;

selecting K eigenvectors associated with K highest eigenvalues from N eigenvectors;

firing K waves weighted by the selected K eigenvectors, each of the selected eigenvector weighting the signals transmitted by the transducers during a firing, these eigenvectors defining a truncated transmission matrix composed of, in a first part, the K eigenvectors of the family of eigenvectors associated with the K highest eigenvalues of the characteristic matrix and, in a second part, columns of zeros corresponding to the firings that are not effected;

receiving the signals returned by the medium;

multiplying a reception matrix constituted of the acquired signals completed by data set to zero corresponding to the firings not effected by the inverse of the transmission matrix to obtain a complete data set;

extracting low-resolution images from the complete data set as in synthetic aperture echographic imaging methods; and reconstructing the high-resolution image corresponding to the area of interest by coherent summing, as in synthetic aperture echographic imaging methods, of the low-resolution images extracted from the complete data set.

* * * * *